United States Patent [19]
Chiari et al.

[11] Patent Number: 5,785,832
[45] Date of Patent: Jul. 28, 1998

[54] COVALENTLY CROSS-LINKED, MIXED-BED AGAROSE-POLYACRYLAMIDE MATRICES FOR ELECTROPHORESIS AND CHROMATOGRAPHY

[76] Inventors: Marcella Chiari, Via G. Brocchi 11; Pier Giorgio Righetti, Via Archimede 114, both of Milan, Italy

[21] Appl. No.: 518,598

[22] Filed: Jul. 26, 1995

[51] Int. Cl.⁶ .................... G01N 27/26; G01N 27/447
[52] U.S. Cl. .................... 204/469; 204/456; 204/606
[58] Field of Search .................... 204/469, 456, 204/606

[56] References Cited

U.S. PATENT DOCUMENTS 4,504,641  3/1985  Nochumson .................... 526/238.2

FOREIGN PATENT DOCUMENTS 9311174  6/1993  WIPO.

OTHER PUBLICATIONS

P. G. Righetti et al, "Towards new formulations for polyamide matrices: N-Acryloyl amino ethoxy ethanol, a novel monomer combining high hydrophilicity with extreme hydrolytic stability" Electrophoresis 15 (1994)* 177–186.
Marcella Chiari et al, "New types of large-pore polyacrylamide-agarose mixed-bed matrices for DNA electrophoresis: Pore size estimation from Ferguson plots of DNA fragments", Electrophoresis 16 (1995)* 1337–1344.

*Primary Examiner*—Kathryn L. Gorgos
*Assistant Examiner*—John S. Starsiak, Jr.
*Attorney, Agent, or Firm*—Fish & Neave

[57] ABSTRACT

Covalently cross-linked, mixed-bed agarose-polyacrylamide matrices for electrophoresis and chromatography are disclosed. The mixed-bed matrices are formed by the copolymerization of a substituted agarose mixture with acrylamide monomers. The disclosed matrices have improved polymerization properties enabling the formation of gels which have higher porosity and elasticity than conventional gels and which are therefore particularly suited to the separation of intermediate size DNA fragments and high molecular mass proteins.

7 Claims, 4 Drawing Sheets

COVALENTLY CROSS-LINKED, MIXED-BED AGAROSE-POLYACRYLAMIDE MATRICES FOR ELECTROPHORESIS AND CHROMATOGRAPHY

The present invention concerns the use of polyacrylamide-agarose mixed-bed matrices, covalently linked, for the separation of fragments of nucleic acids, particularly DNAs of intermediate size (from 50 to 5,000 base pairs) and of high molecular mass proteins (>500,000 Da).

BACKGROUND OF THE INVENTION

The ability to separate and recover DNA is a key component of studies of genetic regulation, genomic sequence, diagnostic analysis and disease control. These procedures require the use of electrophoretic techniques able to resolve mixtures of DNA fragments ranging in size from a few hundred to several million base pairs. In addition, DNA sequencing requires a separation method capable of resolving fragments differing by only a single nucleotide in length. The resolution of intermediate-size DNA fragments is not linear in polyacrylamide gels, whereas the sieving capability of agarose is inadequate and the bands are too diffuse.

Agar matrices (from which agarose is obtained) have been described in zone electrophoresis since 1951 (Peniston, Agar and McCarthy, *Anal. Chem.* 23, 1951, 994–999). One of the most common applications, Immunoelectrophoresis, has been reported already in 1955 by Grabar and Williams (*Biochim. Biophys. Acta* 17 1955, 67–77). Polyacrylamide matrices were introduced as early as 1959 by Raymond and Weintraub (*Science* 130, 1959, 711–712) and subsequently widely promoted for disc electrophoresis by Davis (*Ann. N.Y. Acad. Sci.* 121, 1964, 404–427), Ornstein (*Ann. N.Y. Acad. Sci.* 121, 1964, 321–349) and Hjerten (*J. Chromatogr.* 11, 1963, 66–70).

The success of polyacrylamides as electrophoretic support matrices derives from some fundamental properties, such as: a) optical and UV transparency; b) electrical neutrality, resulting from the absence of charged residues linked to the polymeric chains; and c) ability to form gels with a wide range of porosities. Nevertheless, it is well known that an increase in pore size is achieved in polyacrylamide gels by decreasing the total monomer percentage (% T lower than 2.5%) or increasing the cross-linking concentration (% C, higher than 20%). However, in the first case, the gels are fragile and difficult to handle, whereas in the second case they become hydrophobic and extrude the solvent from the polymeric fibers.

In order to overcome these problems and to obtain matrices of higher porosity, Uriel and Berges (*C.R. Acad. Sci. Paris*, 262, 1966, 164–174; Uriel, U.S. Pat. No. 3,578,604) proposed polyacrylamide-agarose mixed-bed gels, obtained by mixing agarose polymers with acrylamide monomers and an appropriate amount of catalysts. The matrix was obtained by a simultaneous but independent process of agarose and acrylamide gelification leading to an intertwining of the two polymers which, however, were not covalently liked. These mixed-bed gels have been subsequently applied to the separation of nucleic acids by Peackock and Dingman (*Biochemistry* 7, 1968, 668–675).

In a further development, Nochumson described a polyacrylamide-agarose mixed-bed matrix in which the two polymers were cross-liked by means of an activation process of the agarose matrix with allylglycidyl groups. The process used to produce ethylenic, unsaturated polysaccharide resins was, in turn, based on a method already described by Guiseley (U.S. Pat. No. 3,956,273). However, the applicants have realized that the Nochumson process, where agarose substitution takes place by dissolving the polymer in a strongly alkaline solution at high temperature, leads to an uncontrolled degree of substitution of the hydroxyl groups of the sugar monomers, thus forming mixed-bed gels of uncontrolled porosity, leading to irreproducible electrophoretic separations from one batch of activated agarose to another. Furthermore, the aim of the Nochumson invention was not the improvement of the sieving properties of the mixed-bed matrices for specific electrophoretic applications but the production of gel films with improved drying characteristics.

SUMMARY OF THE INVENTION

It has now been found that mixed-bed matrices of the type polyacrylamide-agarose, covalently linked (cross-linked), are useful in the separation of fragments of nucleic acid, particular DNA, of intermediate size (from 50 to 5,000 base pairs) and of high molecular mass proteins (>500,000 Da).

Therefore, the aim of the present invention is to provide covalently-linked polyacrylamide-agarose mixed-bed matrices suitable for use in the separation of fragments of nucleic acids of intermediate size. In accordance with the present invention, covalently-linked polyacrylamide-agarose mixed-bed matrices are formed by copolymerization of agarose mixtures with monomers of formula:

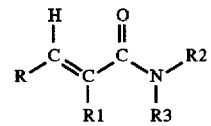

where R and $R_1$, independently among them, represent hydrogen, $C_1$–$C_4$ alkyls or phenyls, whereas $R_2$ and $R_3$, independently among them, represent hydrogen, $C_1$–$C_4$ alkyls containing one or more substituents OH, SH, $OR_4$ or $SR_4$ (where $R_4$ is an alkyl $C_1$–$C_4$ or a hydroxyalkyl $C_1$–$C_4$ and containing one or more atoms of nitrogen to form an heterocyclic ring containing other heteroatoms). The agarose mixtures also comprise agarose derivatized with residues bearing double bonds in a mixture with underivatized agarose. In accordance with a preferred embodiment of the present invention, the agarosic polymer preferably has an average degree of substitution of one allylglycidyl residue per disaccharide base unit and the monomer is N-acryloyl-amino-ethoxy-ethanol.

In one preferred embodiment of the present invention, we propose the use of N-acryloyl-amino-ethoxy-ethanol (AAEE) a novel monomer, highly hydrophilic and extremely resistant to hydrolysis (Chiari, Micheletti, Nesi, Fazio, Righetti; *Electrophoresis* 15, 1994, 177–186), as the base of the polymeric matrix to be coupled to agarose. Moreover, we describe an agarose substitution process which takes place in heterophase, able to produce a polymer with a controlled degree of substitution (one allylglycidyl residue per disaccharide unit), thus allowing the synthesis of mixed-bed gels of controlled porosity with reproducible electrophoretic characteristics. In addition, we describe the determination of the average pore size of these gels and the application of these matrices to high resolution analysis of DNA fragments from 50 to 5000 base pairs in length. The invention also includes the use of other types of mono- and di- substituted acrylamide monomers as well as simple acrylamide and the possibility to use, in the mixed-bed matrices formulations, mixtures of substituted and unsubstituted agarose.

Applicants new mixed-bed matrix presents the following characteristics:

a) Gelling ability even at extreme monomer dilutions (e.g., as low as 1%);
b) Ability to polymerize in the presence of oxygen;
c) Higher porosity and elasticity than conventional pure acrylamide matrices;
d) Unique sieving properties for DNA fragments of intermediate size (from 50 to 5,000 base pairs) and for high molecular mass proteins (500,000 Da).

The advantages of the matrices produced according to the present invention as compared to those presently in use are outlined below. The matrices of the present invention may be used in all the chromatographic and electrophoretic methodologies for industrial purposes, for research and analytical purposes. In particular the disclosed matrices may be used for: electrokinetic separation methods including capillary zone electrophoresis; nucleic acid fractionation and analysis, such as for DNA sequencing, for analysis of PCR products and DNA fragments, either as native or as denatured molecules, either in capillary zone electrophoresis or on gel slabs or gel tubes and in methodologies dedicated to analysis and characterization of large-size proteins; preparation of immobilized pH gradients and isoelectric membranes for isoelectric purification and characterization of proteins and peptides in multichamber electrolyzers equipped with isoelectric membranes; polymerization in the form of beads for chromatographic purposes, including affinity chromatography, gel filtration, ion-exchange chromatography, as support for grafting different types of ligands; and coating rigid spheres of glass or plastic for types of chromatographic techniques in particular, for all HPLC (High Performance Liquid Chromatography) techniques.

DETAILED DESCRIPTION OF THE PREFERRED EMBODIMENTS

Figure 1:
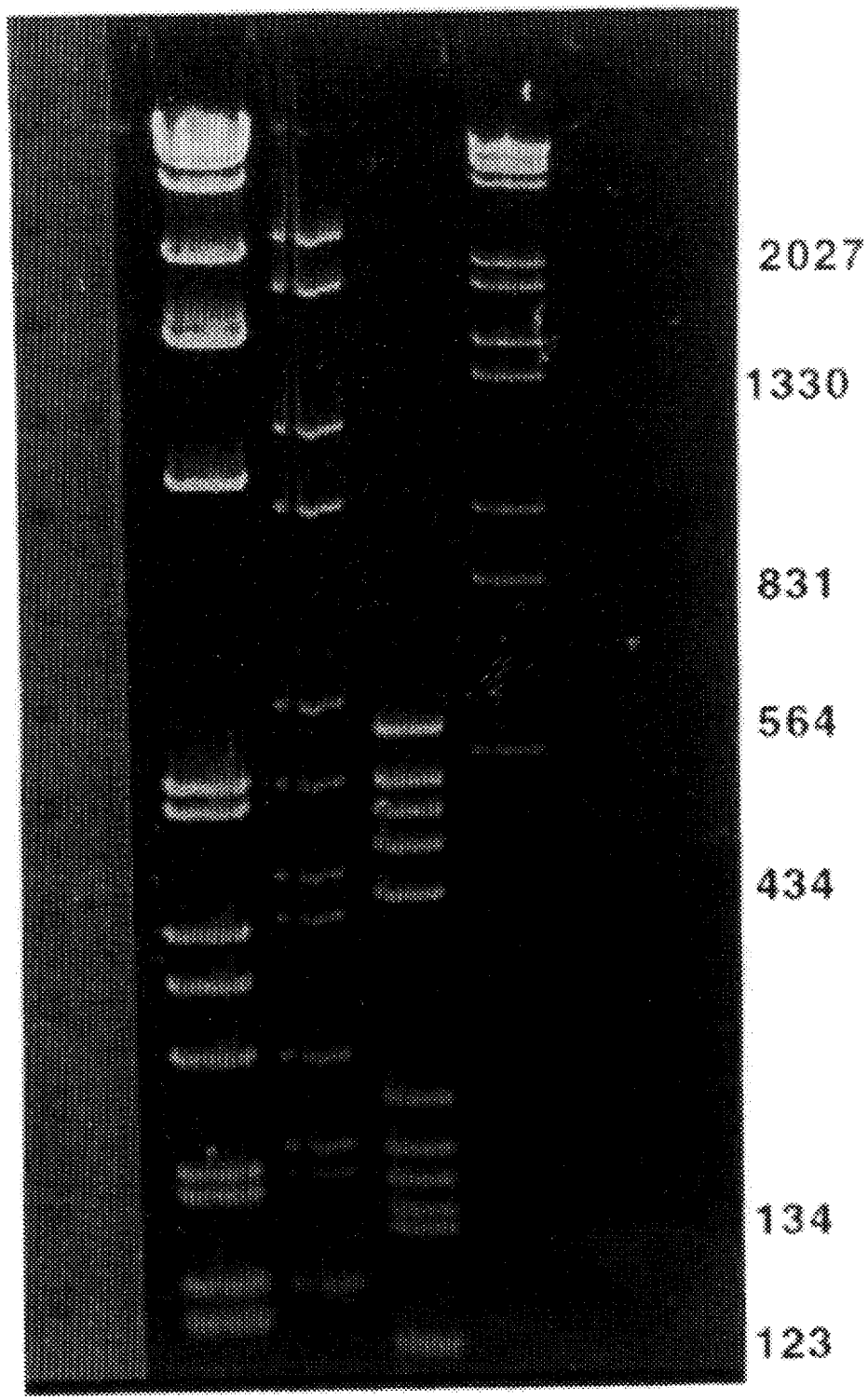
FIG. 1 illustrates an electrophoretic run of DNA molecule mass markers in a typical mixed-bed gel comprising 3% T, 0.4% agarose (⅔ activated, ⅓ normal) cast and run at 10 V/cm for 105 min in TAE buffer. From left to right, the lanes show runs of the following markers: 1) 1 Kb ladder, 2) DNA marker VI, 3) DNA marker V, 4) DNA marker III.

Allylglycidyl derivatized agarose was synthesized with a controlled degree of substitution. 33 mg of sodium borohydride and 1.6 ml of allylglycidyl ether were added under magnetic stirring to a suspension of agarose (1 g) in NaOH (33 ml, 0.3N). After stirring for 12 hours, agarose was recovered from the suspension by filtration and washed with distilled water to neutral pH. The derivatized agarose was dehydrated with methanol and dried in a oven at 35° C. under vacuum.

In order to determine its structure, the compound derivatized as described above, was subjected to NMR analysis. First, the activated agarose was dissolved in DMSO-d6 at 90° C. After complete solubilization the temperature was lowered to 50° C. and all the $^{13}C$ spectra at 50.29 MHZ were acquired on an AM-Bruker wide bore spectrometer. As generally accepted, the basic unit of agarose consists of alternating 3-linked β-D-galactopyranose and 4-linked 3,6-anhydro-a-L-galactopyranose residues. Substituents such as sulfate esters, methyl ethers etc. in different amounts are present. The proton-decoupled $^{13}C$ NMR spectrum of agarose shows the typical resonance of the base unit and also the presence of an ethyl ether in position 6 of the pyranose ring. All the resonances were assigned on the basis of previously reported assignments (Japhe, W. And Lahaye, M., *Carbohydr. Res.* 190, 1989, 249–265). In the proton decoupled $^{13}C$ NMR spectrum of activated agarose the two characteristics signals of methyne carbons are present in a separate region (resonances of $C_1$ and $C_2$ referred to DMSO signals: 116.05 ppm and 135.27 ppm respectively) and therefore were used for quantitative determination with respect to the anomeric signals.

All the proton-decoupled spectra were acquired with sufficient relaxation delay (30 sec) in order to justify the integration of signals. The regions of anomeric resonances and methyne carbons were integrated separately. The ratio between the two integrated regions gives the amounts of the allylglycidyl-ether insertion, which indicates one molecule per one base dimer. Resonances of $C_1$ and $C_2$ referred to DMSO signals: 116.05 ppm and 135.27 ppm respectively.

Substituted agarose produced by this method dissolved at 70°–75° C., gelified at 31° C. and redissolved at 58°–60° C. The product known in the technique having a higher degree of substitution redissolved at 30°–35° C.

Mixed-bed gels were cast between glass plates and run in a vertical slab gel apparatus, according to a procedure typically employed for polyacrylamide gels, or cast and run in a horizontal system; in this case the polymerization and the run took place "at open face" according to a procedure classically used for agarose gels. In the vertical apparatus (15×16×0.8 cm) slab gels were employed. In the horizontal technique the gels are 1 cm thick and have a loading capacity at least 5 times higher than vertical gels. In both cases the gelling solution was prepared as follows: the desired amount of a mixture of activated agarose and normal agarose (ratio 2:1) was dissolved at 95° C. in Tris-acetate EDTA (89 mM Tris, 2 mM EDTA, pH 8.0), the solution was cooled to 50° C. under stirring. The desired amount of acrylamide monomer was then added and the volume was adjusted to the final value. 0.3 μl per ml of TEMED and 0.08 μl per ml of ammonium persulfate (from a stock at 40%) were then added and the solution was mixed and quickly poured into the previously prepared gel mold. Gelation usually occurred within 5-10 min, depending on the acrylamide concentration.

The following formulations have been used for vertical gels.

Acrylamide monomer concentration from 1.5 to 12% and agarose concentration from 15 to 4% given as w/w (% of agarose in weight over the weight of the acrylamide derivative). In a typical vertical gel example, 0.4 g of agarose (a mixture of 0.133 g not activated and 0.267 g activated) were added to 100 ml of a 10% acrylamide solution.

In horizontal gels a typical formulation was an acrylamide monomer concentration of about 3% w/v and an agarose concentration of about 0.5% w/v.

FIG. 1 shows the separation of DNA fragments (from 50 to 5000 base pairs, bp) in a mixed-bed gel consisting of 4% T AAEE monomers, in the presence of 0.4% agarose (a mixture of ⅔ activated and ⅓ not activated agarose). It can be seen that an optimal separation is achieved for both smaller and larger DNA fragments, up to 5,000 bp.

Figures 2A, 2B, 2C:
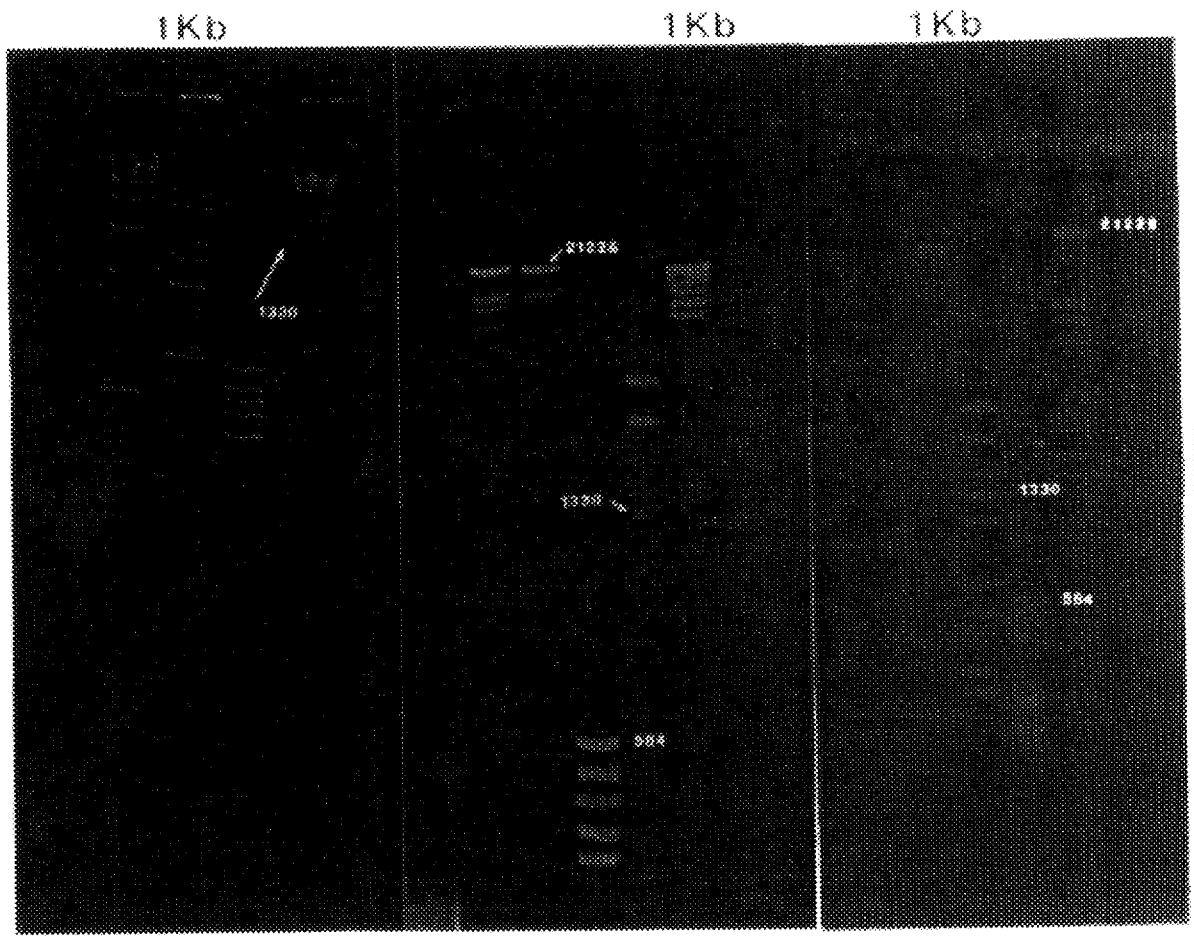
FIG. 2 shows an electrophoretic run of DNA fragments in three different types of gels: A) a standard polyacrylamide gel (4% T 3.3% C), B) a mixed-bed gel containing 2% acrylamide, 10% agarose (expressed as w/w of poly-AAEE); and C) a 1.2% agarose gel. The conventional polyacrylamide gel was run at 10 V/cm for 200 min, the mixed-bed gel was run at 6.5 V/cm for 300 min, the agarose gel was run at 4 V/cm for 195 min. The samples were as follows: 1) DNA marker III; 2) DNA marker V; 3) DNA marker VI; and 4 and 4b) 1 Kb ladder.

FIG. 2 shows the separation of DNA molecular mass fragments in three types of gels: standard polyacrylamide (gel A consisting of 4% T and 3.3% C; mixed-bed gels according to the present invention (gel B, consisting of 4% AAEE 10% agarose; the latter expressed as %, w/w, of the total AAEE content, namely 4% T); standard agarose (gel C consisting of 1.2% agarose). It can be seen that the gel A, able to finely sieve small DNA fragments, up to 1000 bp, does not allow the migration of fragments having a size higher than 5,000 bp, which precipitate at the application point. In comparison, the mixed-bed matrix (gel B), provides good resolution of fragments of a few hundred bp in length and also allows the migration of larger DNA fragments up to 21,226 bp in length. The agarose gel (matrix C), shows a good separation of large size fragments (from 5,000 to 21,226 bp) but does not allow a good resolution of small fragments (for instance, the DNA fragments from 100 to 564 bp present very diffuse and poorly resolved bands). Therefore, the mixed-bed gel of the present invention presents unique sieving properties in the DNA size interval ranging from 50 to 5000 bp, an interval of extreme interest for both human genome sequencing and for DNA fragments obtained via PCR (polymerase chain reaction) techniques, today largely utilized for screening of genetic diseases and in forensic medicine.

Figures 3A, 3B:
FIG. 3 shows an electrophoretic run of DNA fragments in two types of gels: A) a 2% agarose gel; B) a mixed-bed gel comprising 4% T poly-AAEE and 10% agarose (the latter expressed as a percentage, w/w, of poly-AAEE). Both gels were cast and run in a horizonal submarine system. The agarose gel was run at 4 V/cm in TAE buffer for 180 min, the hybrid gel was run at 6.5 V/cm for 240 min. The samples were as follows: 1) KB ladder; 2) DNA marker VI; 3) DNA marker V; and 4) DNA marker III. The gels were stained with ethydium bromide.

An additional demonstration of the optimal degree of resolution obtained in mixed-bed matrices is presented in FIG. 3, showing an electrophoretic separation performed in a horizontal, open face system, a so-called submarine gel (because the run takes place under a film of buffer). The gel on the right contains 2% agarose, whereas the matrix on the left is a mixed-bed matrix (4% T, 10% agarose, w/w, over the percentage of AAEE monomer). One can note again the optimal resolution in the 100-600 bp interval achieved in the mixed-bed gels compared to the agarose gels (in spite of the concentration increase to 2% compared to the 1.2% of FIG. 2). The ability to obtain such a good resolution in this type of horizontal electrophoretic runs is extremely important since submarine gels are largely preferred to vertical electrophoresis with the gel sandwiched between two glass slabs. It should be noted, additionally, that the gel has been polymerized as an open-face system, i.e. bound to only a single glass slab, as routinely done for plain agarose gels. This indicates that the polymerization of these gels is not influenced by atmospheric oxygen (contrary to pure polyacrylamide gels, where it is essential to exclude oxygen to achieve the polymerization).

Figure 4:
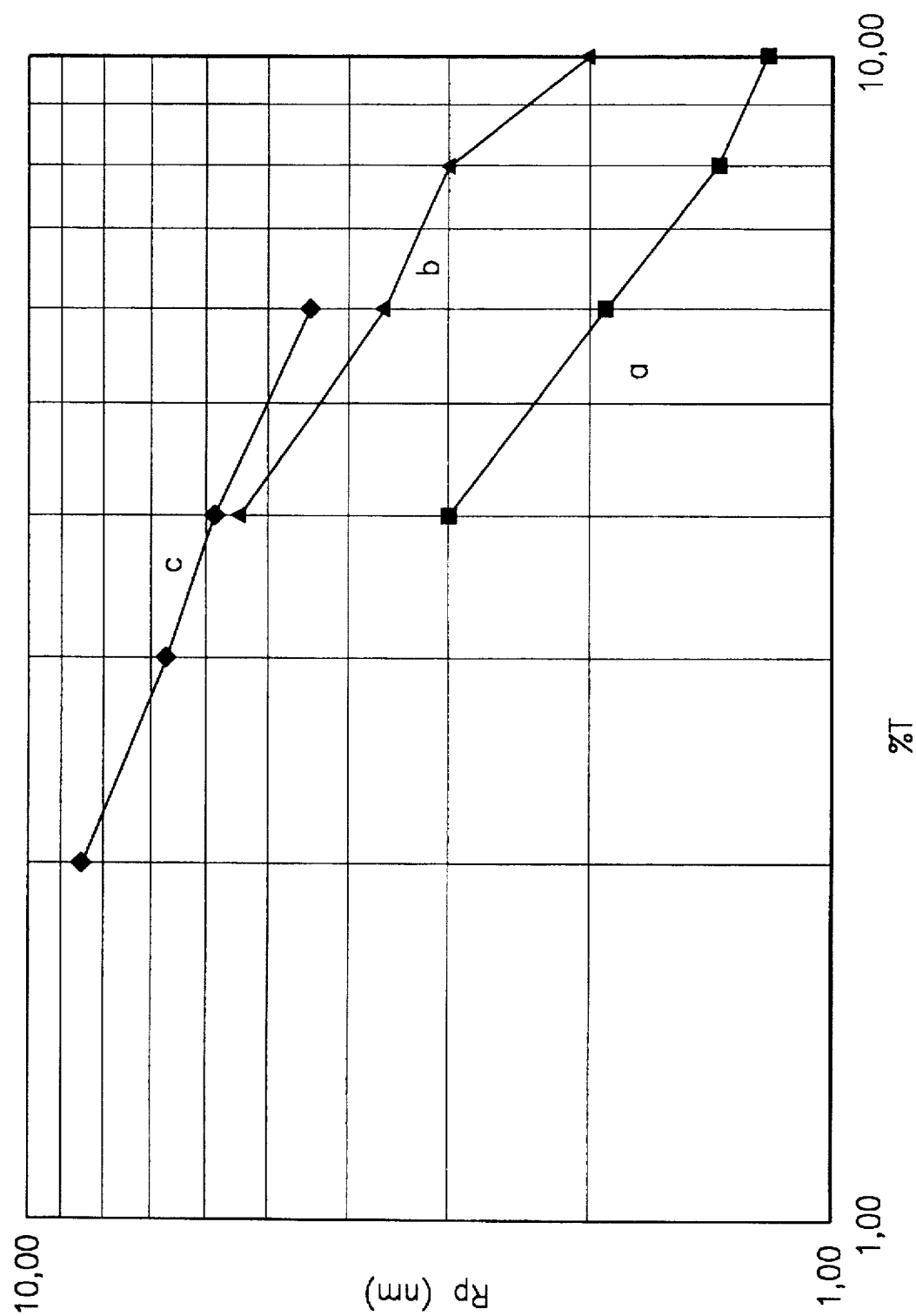
FIG. 4 depicts the average porosity determination for different types of gels as a function of the poly-AAEE percentage. The log—log plot represents the dependence of the apparent gel pore size, $R_p$, as a function of poly-AAEE concentrations. Curve (a) shows 3.3.% Bis cross-linked poly-AAEE gels; curve b) shows mixed-bed gels with 4.7% agarose as w/w of AAEE; and curve c) shows hybrid gels with 10% of agarose (w/w of AAEE). Geometric radius, $R_1$ was used for DNA size measurement. The slope values of the straight lines extrapolated, by linear regression, from the experimental values are: a) $-1.025$; b) $-1.1$; and c) $-0.63$.

From the electrophoretic behavior (FIGS. 1-3) it was shown that the porosity of agarose-polyacrylamide mixed-bed gel must be, somehow, intermediate between those of pure acrylamide (typically low-porosity gels) and agarose matrices (a typical class of high-porosity gels). A precise evaluation has been obtained by measuring the limit mobility of DNA fragments migrating in gels of different monomer concentration (% T) or in mixed-bed matrices, as shown in FIGS. 1-3. According to the extended Ogston theory, the macromolecular size of a DNA fragment having a mobility equal to one-half its mobility at zero gel concentration represent the average pore size value of the gels where the migration took place. The results are shown in the double-log plot of FIG. 4 where % T represent the monomer concentration and $R_p$ the pore diameter. Curve (a) gives the pore size values in polyacrylamide gels (bis-acrylamide cross-linked gels) in the interval from 4 to 10% T (at 3.3% C), representing the control. Curve (b) presents the same dependency for mixed-bed gels containing 4.7% of agarose over the same amounts of poly-AAEE (from 4% T to 10% T). In this case it can be seen that the pore size values range from 5.5 nm to 2 nm, with an increase in porosity of about 100%. When the agarose concentration is increased to 10% (over the % T) a further increase in the porosity is obtained at very low % T values, as represented in curve © (at such a low % T values a normal poly-AAEE gel does not gel any more). For instance, a 2% T poly-AAEE mixed-bed gel has an average porosity of 8.5 nm, a value 3 times higher than that of a classical diluted polyacrylamide gel. In spite of the low monomer content, these highly porous gels are extremely elastic and easy to handle.

While the invention has been explained in relation to its preferred embodiments, it is to be understood that various modifications thereof will become apparent to those skilled in the art. The foregoing disclosure is not intended or to be construed to limit the present invention, or to otherwise exclude any such other embodiments, adaptions, variations and equivalent arrangements, the present invention being limited only by the claims appended hereto and the equivalents thereof.

We claim:

1. A mixed-bed matrix for electrophoresis comprising covalently-linked polyacrylamide-agarose formed by the copolymerization of at least one monomer with an agarose mixture of allyl-agarose with a gelling point not lower than 35 C and underivatized agarose;

wherein said at least one monomer has the following general formula:

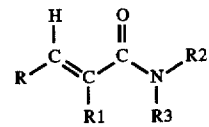

wherein R is hydrogen, $C_1$–$C_4$ alkyls or phenyls;
wherein $R_1$ is hydrogen, $C_1$–$C_4$ alkyls or phenyls;
wherein $R_2$ is hydrogen or $C_1$–$C_4$ alkyls bearing one or more substituents OH, SH, $OR_4$ or $SR_4$ where $R_4$ is an alkyl $C_1$–$C_4$ or hydroxyalkyl $C_1$–$C_4$ and interrupted by one or more atoms of nitrogen to form an heterocyclic ring;

wherein $R_3$ is hydrogen or $C_1$–$C_4$ alkyls, bearing one or more substituents OH, SH, $OR_4$ or $SR_4$ where $R_4$ is an alkyl $C_1$–$C_4$ or hydroxyalkyl $C_1$–$C_4$ interrupted by one or more atoms of nitrogen to form an heterocyclic ring; and wherein said agarose mixture comprises agarose derivatized with residues bearing double bonds.

2. The mixed-bed matrix of claim 1 wherein said agarose mixture comprises agarose and derivatized agarose and wherein the weight of agarose is no more than one half of the weight of derivatized agarose.

3. A mixed-bed matrix for electrophoresis comprising covalently-linked polyacrylamide-agarose formed by the copolymerization of at least one monomer with an agarose mixture;

wherein said at least one monomer comprises N-acryloyl-amino ethoxy-ethanol; and wherein said agarose mixture comprises agarose derivatized with residues bearing double bonds.

4. The mixed-bed matrix of claim 3 wherein said agarose derivatized with residues bearing double bonds comprises agarose derivatized with allylglycidyl ether.

5. The mixed-bed matrix of claim 4 wherein said derivatized agarose bears an average degree of substitution of 1 residue of allylglycidyl per disaccharide unit.

6. A mixed-bed matrix comprising covalently linked polyacrylamide-agarose formed by the copolymerization of N-acryloyl-amino ethoxy-ethanol and agarose derivatized with allylglycidyl ether.

7. The mixed-bed matrix of claim 6 wherein said agarose bears an average degree of substitution of 1 residue of allylglycidyl per disaccharide unit.

* * * * *